(12) United States Patent
Risi et al.

(10) Patent No.: US 7,587,248 B2
(45) Date of Patent: Sep. 8, 2009

(54) IMPLANTABLE PROSTHETIC DEVICE

(75) Inventors: Frank Risi, Newtown (AU); Peter Gibson, South Coogee (AU); Ya Ling Tam, Edenson Park (AU)

(73) Assignee: Cochlear Limited, Lane Cove (AU)

( * ) Notice: Subject to any disclaimer, the term of this patent is extended or adjusted under 35 U.S.C. 154(b) by 185 days.

(21) Appl. No.: 11/108,641

(22) Filed: Apr. 19, 2005

(65) Prior Publication Data

US 2005/0234535 A1 Oct. 20, 2005

Related U.S. Application Data

(60) Provisional application No. 60/562,987, filed on Apr. 19, 2004.

(51) Int. Cl.
*A61N 1/04* (2006.01)

(52) U.S. Cl. ..................................... 607/137

(58) Field of Classification Search ............. 607/55–57, 607/137; 623/10
See application file for complete search history.

(56) References Cited

U.S. PATENT DOCUMENTS

| 5,123,422 | A | * | 6/1992 | Charvin | 607/137 |
| 5,653,742 | A | * | 8/1997 | Parker et al. | 607/137 |
| 6,374,143 | B1 | * | 4/2002 | Berrang et al. | 607/137 |

FOREIGN PATENT DOCUMENTS

| CA | 1323731 | 11/1993 |
| EP | 0 002 068 | 12/1981 |
| EP | 0 215 726 A2 | 3/1987 |

* cited by examiner

*Primary Examiner*—Carl H Layno
*Assistant Examiner*—Yun Haeng Lee
(74) *Attorney, Agent, or Firm*—Connolly Bove Lodge & Hutz LLP (57) ABSTRACT

An implantable device having an elongate electrode carrier with a longitudinal axis, the carrier having at least one electrode mounted in the electrode carrier so as to provide exposure to the exterior of the electrode carrier, and at least one closed break in the surface of the electrode carrier arranged to allow flexing of the electrode carrier.

44 Claims, 7 Drawing Sheets

IMPLANTABLE PROSTHETIC DEVICE

CROSS-REFERENCE TO RELATED APPLICATIONS

This application claims the priority of U.S. Provisional Patent Application No. 60/562,987 entitled "Slit Electrode," filed on Apr. 19, 2004. The entire disclosure and contents of the above application is hereby incorporated by reference herein.

BACKGROUND

1. Field of the Invention

The present invention relates generally to an implantable prosthesis and, more particularly, to a prosthetic device having an electrode carrier.

2. Related Art

There are several electrical stimulation devices that use an electrical signal to activate nerve or muscle fibers in a patient to stimulate an activity. A prosthetic hearing device or implant is an example of such a device that is used to aid patients who have a hearing deficiency. Prosthetic hearing devices apply a stimulating signal to the cochlea of the ear to stimulate hearing.

Prosthetic hearing devices need to be rigid enough to maintain their structural integrity and their position, so that electrodes in the device can remain in place against nerve endings. However, insertion or implantation of such prosthetic devices can be uncomfortable and potentially damaging to the delicate physical structures of a body. Therefore, it is desirable to be able to insert the prosthetic hearing device in a manner that does not damage delicate physical structures while maintaining the structural integrity of the device.

CA 1323731 (Societe Anonyme MXM) describes an electrode-carrier device able to be implanted in the cochlea so as to electrically stimulate the nervus acusticus. It is directed to the problem of aligning the electrodes in the electrode carrier against the nerve ends in the cochlear. The cochlear, being a helicoidal tube, twists any electrode carrier being inserted into it and so the insertion raises alignment issues. To achieve the aim of aligning the electrodes against the nerve ends, the electrode carrier of this disclosure includes a mechanical discontinuity extending over only one part of the cross-section, dissymmetric to the axis of the carrier and close to the extremity of the carrier. The mechanical discontinuity is limited to the lateral and medial sides of the electrode carrier.

EP 0 002 068 B1 (Hansen et al) describes an electrode carrier in which the part to be accommodated in the cochlear has an eigencurvature in the longitudinal direction of the support. During implantation, the carrier is forced to assume a temporary condition of curvature. After implantation, the carrier is transferred from the temporary curvature to a permanent curvature by mechanical means. Therefore, the material used for the carrier must be a material with mechanical memory.

SUMMARY

In one aspect of the invention, an implantable device is disclosed. The implantable device comprises: an elongate electrode carrier having one or more breaks disposed in a surface of the carrier, wherein the one or more breaks are arranged to allow the electrode carrier to flex in any direction away from the longitudinal axis; and at least one electrode mounted in the electrode carrier.

In another aspect of the invention, a prosthetic hearing device is disclosed. The device comprises: an elongate electrode carrier having one or more breaks disposed in a surface of the carrier, wherein the one or more breaks are constructed and arranged to reduce at least one of either surface tension and compressive force of the electrode carrier when the electrode carrier is flexed or bent away from the longitudinal axis; and at least one electrode mounted in the electrode carrier.

In a further embodiment, a method of manufacturing an implantable device having an electrode carrier with a longitudinal axis. The method comprises: forming the electrode carrier; mounting an electrode in the carrier; and forming at least one break in the carrier, wherein the at least one break is arranged to allow the electrode carrier to flex in any direction away from the longitudinal axis.

BRIEF DESCRIPTION OF THE DRAWINGS

The invention will be described in conjunction with the accompanying drawings, in which.

DETAILED DESCRIPTION

An electrode carrier according to embodiments of the present invention may have incorporated, either before or after assembly, circumferential or linear breaks along part or the entire length of the electrode carrier. Any number or arrangement of breaks may be contained either in-between stimulating ring(s)/pad(s), i.e., electrodes, (see, for example, the illustrative embodiment shown in FIG. 1), or along the entire length over the electrodes (see, for example, the illustrative embodiment shown in FIG. 2), in a circumferential or linear pattern.

Embodiments of the present invention are described below in connection with one embodiment of an exemplary implantable medical device, a hearing prosthesis. Specifically, the exemplary application is a cochlear™ implant system (also referred to as a cochlear™ prosthesis, cochlear™ prosthetic device and the like; "prosthetic hearing device" herein). Prosthetic hearing devices use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a prosthetic hearing device provides stimulation of the cochlear nucleus in the brainstem. It should be appreciated, however, that embodiments of the present invention ma be applied to and/or constructed and arranged to be used in any appropriate electrical stimulating device.

For the purposes of the preferred embodiment, the term "breaks" should be construed broadly to include one or more breaks in any configuration or arrangement, as long as the breaks provide a cut, cut-out, slit, slice, or other similar surface modification (collectively and generally referred to as "breaks" herein) to any portion of an electrode carrier that reduces the surface tension and/or compressive forces of the electrode carrier when the electrode carrier is flexed or bent.

Breaks may be defined as cuts made in the electrode carrier material, or any other feature that acts to create a series of small, discrete surfaces, as opposed to one continuous surface. The breaks may also be introduced on the molding of the electrode carrier. The breaks may be an "open cut" achieved by moulding, or the removal or modification of material, or a "closed cut" which uses a much softer/flexible material, or a material that restricts compression but facilitates stretching and replaces the removed or modified carrier.

Suitable breaks include but are not limited to "V", "W", "U", "X", etc. shaped regions, circumferential and/or linear sections, ribbed and/or corrugated surfaces, helical and/or screw thread sections, etc. in either symmetrical and/or non-symmetrical fashion.

Electrode carriers are often made out of silicone. One advantage of a corrugated type surface is reduced frictional force, due to reduced adhesive contribution, between the electrode carrier and the structure of the cochlear. Silicone friction on smooth substrates, such as the surface of a cochlear, has two contributors: adhesive or surface, and hysteretic or bulk. Surface friction results from the attractive force between the silicone and the smooth substrate. Using lubricant does not assist in this case as the smooth surfaces do not provide a suitable path for the lubricant and can, in fact, lead to an increase in the attraction between the two surfaces. This increases the difficulty of, for example, inserting an electrode carrier into a cochlear.

In the cochlear, the fragile basilar membrane and spiral ligament of the cochlear are very smooth. With a silicone carrier, the attraction between the carrier and the basilar membrane or spiral ligament may result in nearly complete contact at the interface, resulting in large sliding friction forces. For rough surfaces, such as that provided by a corrugated surface or other break to the surface of the electrode carrier, the adhesive contribution to the frictional force will be much smaller due to the reduced surface contact. Therefore, the frictional force will mostly be a result of the bulk friction. This reduction in friction force facilitates the insertion of the electrode carrier and reduces the risk of damage to either the basilar membrane or spiral ligament.

Figure 3A:
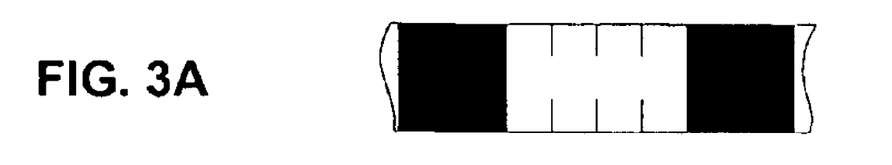
FIGS. 3A, 3B, 3C, 3D, 3E and 3F show exemplary break arrangements in accordance with embodiments of the present invention.
Figure 3B:
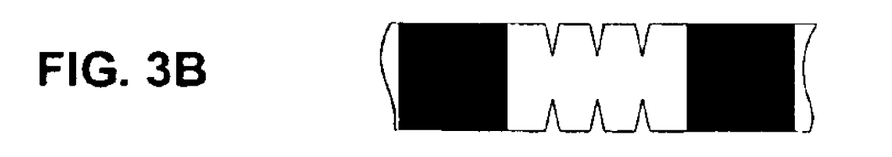
Figure 3C:
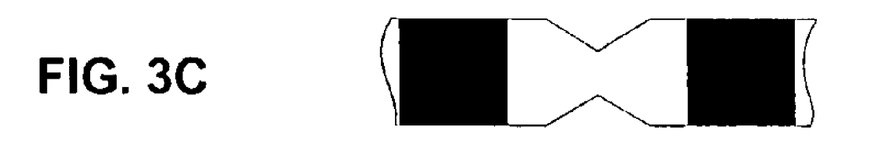
Figure 3D:
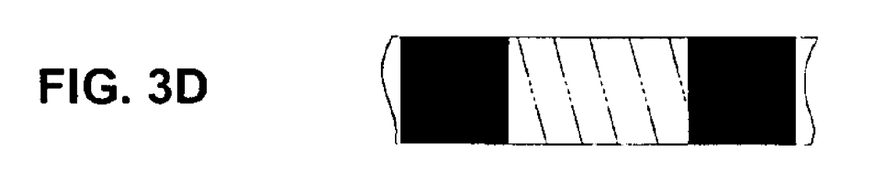
Figure 3E:
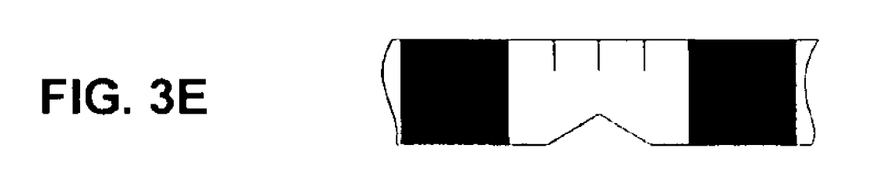
Figure 3F:
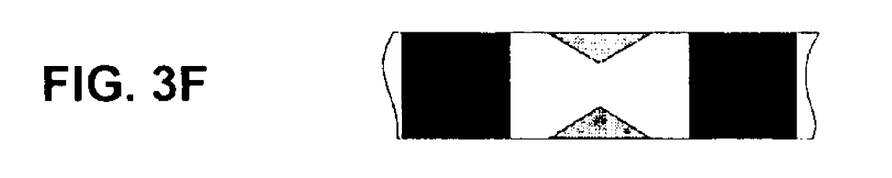

FIGS. 3A, 38, 3C, 3D and 3E provide examples of breaks and break arrangements according to various embodiments of the present invention. FIG. 3F provides one example of a break arrangement combining a stiffer carrier material to maintain axial stiffness in conjunction with a much softer/flexible material to facilitate curvature. Multiple additional examples and combinations may be made in accordance with the present invention, or in light of the present teachings, and should be considered part of the present invention.

Figure 1:
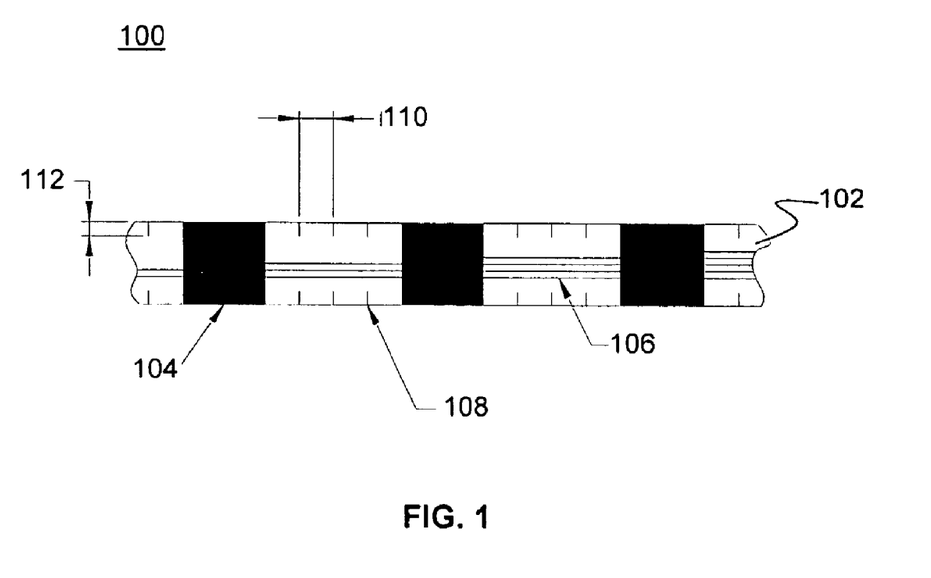
FIG. 1 shows a cross-sectional side-view of an implantable device and associated components in accordance with an embodiment of the present invention.

FIG. 1 shows a cross-sectional side-view of an implantable device 100 and associated components in accordance with an embodiment of the present invention. Implantable device 100 is composed of an electrode carrier 102 with electrodes 104 and electrical conductors 106. Breaks 108 are shown on an upper surface and a lower surface of electrode carrier 102, which may also be representative of circumferential breaks, i.e., breaks that extend around the circumference of implantable device 100. Breaks 108 have a space between breaks as shown by 110 and a depth as shown by 112. It should be appreciated that the represented space between breaks and the depths are exemplary and may be modified in accordance with the present description, or in light of the present teachings, and such modifications or alterations should be considered part of the present invention. Breaks of the present invention may be in any number, depth, spacing, combination, orientation, or arrangement. In embodiments of the present invention, breaks are preferably constructed in a manner that maintains or preserves the hermetic seal of the implantable device.

Figure 2:
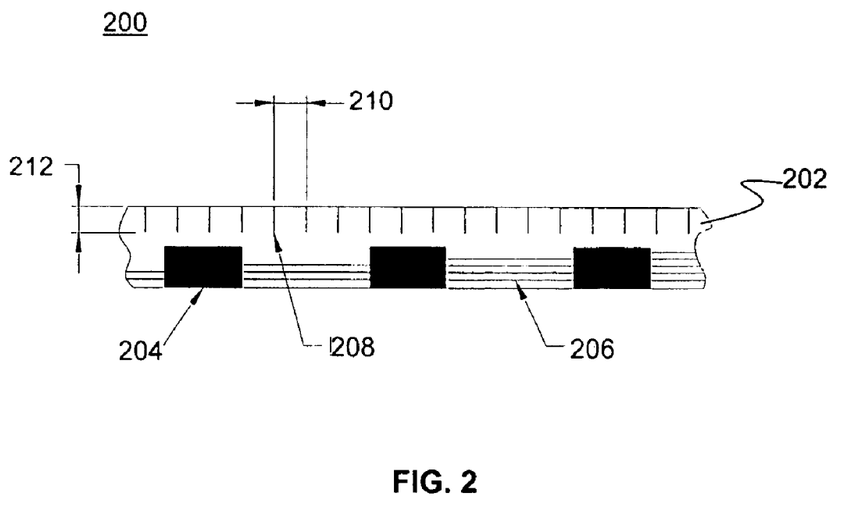
FIG. 2 shows a cross-sectional side-view of an implantable device and associated components in accordance with an embodiment of the present invention.

FIG. 2 shows a cross-sectional side-view of an implantable device 200 and associated components in accordance with another embodiment. Implantable device 200 comprises an electrode carrier 202 with electrodes 204 and electrical conductors 206. Breaks 208 are shown on an upper surface of electrode carrier 202. Breaks 208 have a space 210 between them and a depth 212. It should be appreciated that the represented space between breaks and the depths are exemplary only and may be modified in accordance with the present description, or in light of the present teachings, and such modifications or alterations should be considered part of the present invention. As noted elsewhere herein and as one of ordinary skill in the art would appreciate, breaks of the present invention may be in any number, depth, spacing, combination, orientation, or arrangement. In embodiments of the present invention, breaks are preferably constructed in a manner that maintains or preserves the hermetic seal of the implantable device.

In certain applications, the electrode carrier has a tip member at one end and an implanted stimulator unit at the opposed end. In such application, embodiments of the present invention may provide for breaks to occur near one or both ends and are not limited to having breaks in the portion of the electrode carrier that has the electrodes.

Stimulating ring(s)/pad(s) or electrodes of the present invention may be any standard or custom electrode now or later developed. In embodiments of the present invention, electrodes may be oriented within, or protruding from, an electrode carrier such that the electrodes have direct contact with, or exposure to, a neuron, nerve or nerve ending to which a signal is to be communicated by the implantable device.

Electrical conductors of the present invention, which are typically in the form of wires, may be formed from a suitable electrically-conducting metal. Preferably, the conductors are formed from a suitable biocompatible electrically-conducting material. It should be appreciated that other suitable electrically-conductive materials for use as conductive pathways through electrode carriers of the present invention may be used. For example, in alternative embodiments, semi-conducting materials and electrically-conducting polymers may be used.

In an exemplary embodiment of the present invention, an electrode is housed in an electrode carrier for use as a prosthetic hearing device. As the prosthetic hearing device is inserted into the cochlea the prosthetic hearing device is required to bend sharply in one plane (within a radius of between approximately 1 to 3 mm) and also in a plane perpendicular to that by a distance of approximately 3 mm. By incorporating the noted breaks along the length of the electrode carrier, the straight-to-curved transition is achieved more easily as the surface tension (and compression) of the electrode carrier is distributed over much smaller sections therefore reducing the total force required to insert the prosthetic hearing device to overcome the surface tension and compression to achieve a curved state (see FIG. 4).

Figure 4:
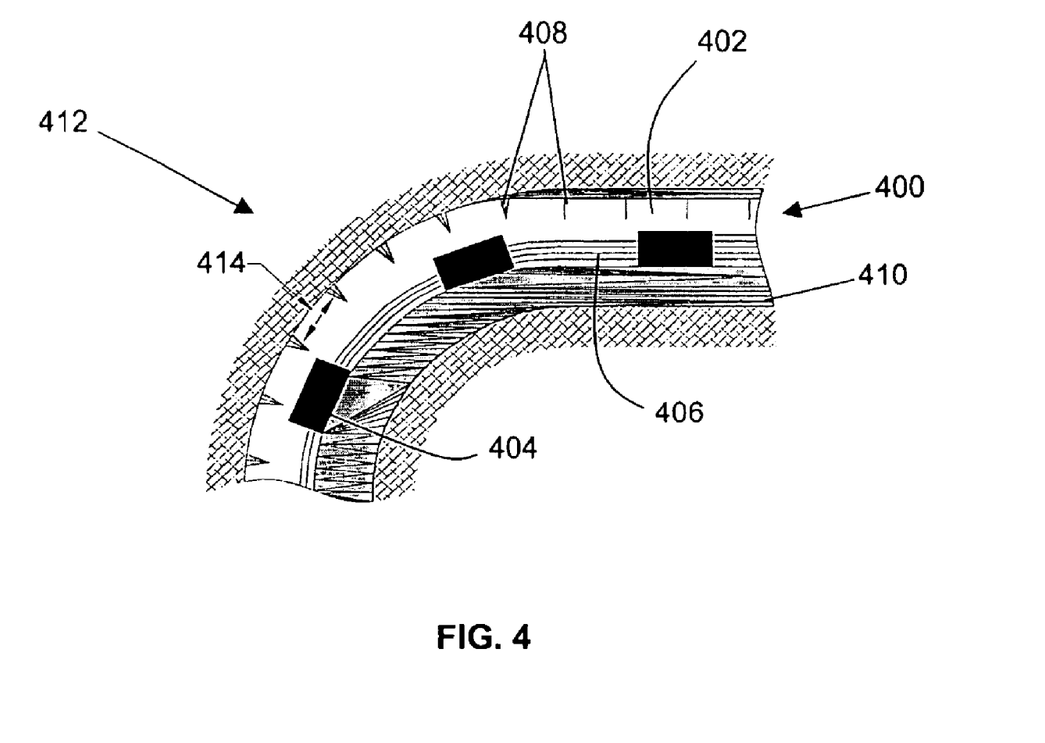
FIG. 4 shows a cross-sectional side-view of an implantable device and associated components in accordance with an embodiment of the present invention inserted into a canal.

FIG. 4 shows a cross-sectional side-view of an implantable device 400 and associated components in accordance with an embodiment of the present invention inserted into a canal 410. In FIG. 4, implantable device 400 is composed of an electrode carrier 402 with electrodes 404 and electrical conductors 406. Breaks 408 are shown on an upper surface of electrode carrier 402. In region 412, implantable device 400 is bent or flexed in canal 410 such that the surface tension on implantable device 400 is reduced at, for example, region 414.

Figure 5A:
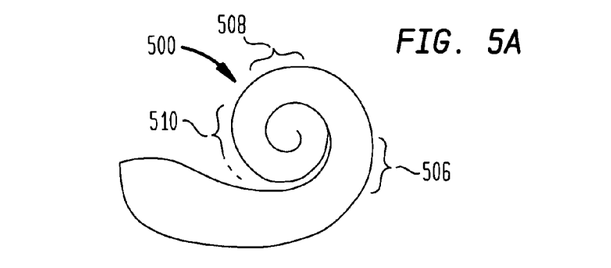
FIG. 5A is a schematic diagram of a cochlear illustrating various positions within the cochlear.
Figure 5B:
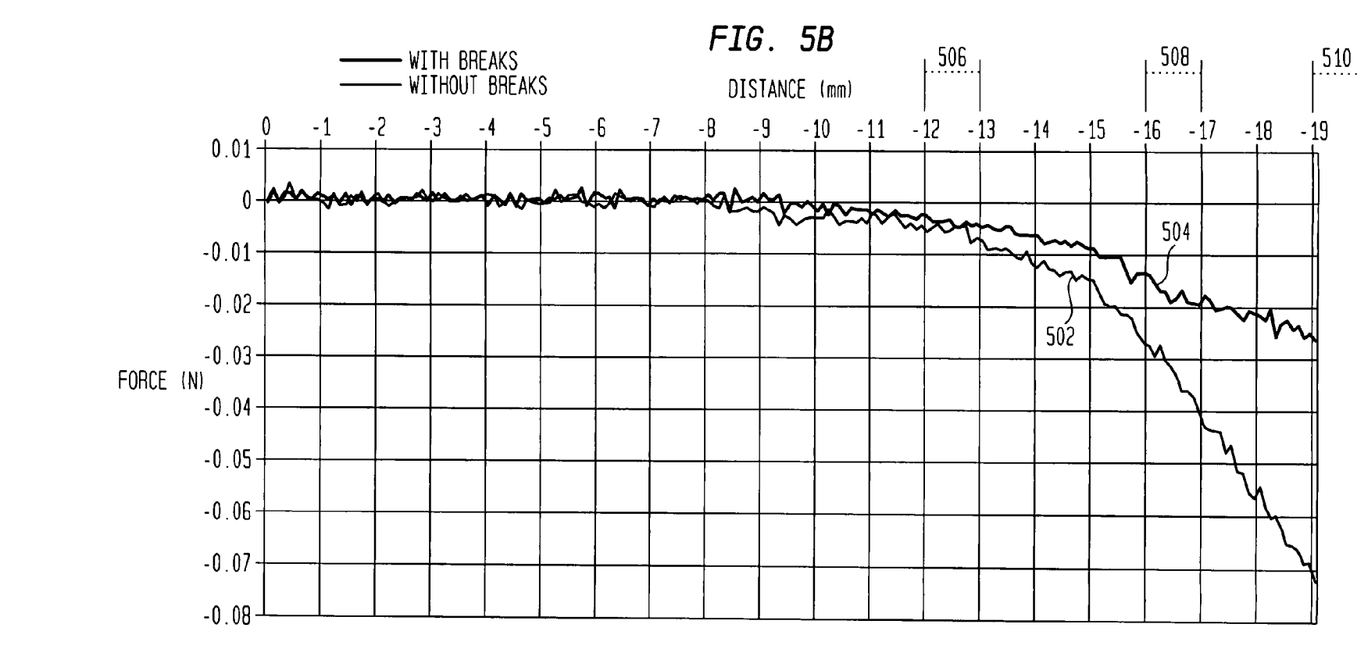
FIG. 5B shows a graphical comparison of the insertion force versus distance of insertion of an electrode carrier into a cochlear without a break to an electrode carrier with a break.

FIG. 5A is a schematic diagram of a cochlear illustrating various positions within the cochlear. FIG. 5B is a graph of the insertion force versus insertion distance of an electrode carrier into a cochlear. The break in this example is linear slits such as those illustrated in FIG. 4. In FIG. 5B, curve 502 indicates the insertion force required to implant an electrode carrier that is not constructed with breaks in accordance with the present invention, while line 504 indicates the insertion force required to implant an electrode carrier that is constructed with breaks in accordance with the present invention.

On insertion of the electrode carrier to position 506 (12 to 13 mm) as shown in the schematic 500 of a cochlear in FIG. 5A, there is not much difference in the insertion force of the two electrode carriers. This is to be expected as there is not much curvature in the cochlear up to this position. After this position in the cochlear, the insertion force between the two electrode carriers starts to diverge.

By position 508 (16-17 mm), the electrode carrier without a break has a much higher insertion force than the electrode carrier with a break. This increases the chance of damage to the cochlear when inserting the electrode carrier without a break. On reaching the inner part of the cochlear (19 mm), the insertion force of the electrode carrier without the break is more than double the electrode carrier with the break.

The electrode carrier with the break gives the electrode carrier flexibility in any direction away from the longitudinal axis of the electrode carrier. On insertion, the electrode carrier must bend around the axis of the cochlear as it is inserted as well as along the axis as it travels from the basal to apical region of the cochlear. Flexibility in the axial direction results in less risk of damage to the fragile cochlear.

Electrode carriers of the present invention may be constructed from any suitable material for implant devices, including, but not limited to, silicone, plastic etc. In one embodiment, the material is biocompatible. According to embodiments of the present invention, breaks may be formed during, after or before assembly of the electrode or electrode carrier. For example, the electrode carrier may consist of a preformed silicone tube (including the breaks), which would have the electrodes and electrical conductors already assembled. Alternatively, the breaks may be part of a molding die that transfers the features to the electrode carrier when the assembled components are molded together, for example, in silicone. Alternatively, the breaks may be formed after the assembly is completed using cutting tools, lasers or chemicals. Any other suitable manufacturing processes now or later developed may be utilized to provide an electrode carrier with a break or breaks.

The above and other exemplary embodiments of the present invention improve flexibility, whilst maintaining a certain degree of axial stiffness, of an implantable electrode device by incorporating features in the profile/shape/dimensions of the electrode carrier that act to reduce surface tension and/or compressive forces as an implantable device curves, thus improving ease of insertion into, for example, the cochlea thus reducing the risk of damage trauma to the delicate physical structures of a body. The present invention may provide circumferential or linear breaks in the electrode carrier that result in the tensile forces on the lateral surface of the electrode device being distributed over much smaller sections, rather than the entire length of the device. Similar features on the medial side of the electrode carrier result in compressive forces being minimized due to a reduction in the amount of material along that surface. For example, when utilized in a prosthetic hearing device, breaks in an electrode carrier constructed according to the present invention will improve an electrode carrier's progress from the basilar turn to the apical turn during insertion as the electrode device becomes flexible in three dimensions, thus reducing the risk of perforating the basilar membrane, whilst maintaining axial stability during insertion.

When utilized in a prosthetic hearing device, an embodiment of the present invention provides increased flexibility of the implantable device to: 1) improve ease of insertion, 2) reduce the risk of damage to the structures of the cochlea, 3) reduce lateral wall forces on the cochlea, and 4) provide minimal insertion trauma for electro-acoustic stimulation.

Embodiments of the present invention have been described in connection with a prosthetic hearing device. However, the present invention may be implemented in any electrical stimulating device, or similar implantable device, now or later developed. The present invention is particularly beneficial when implemented in medical devices. Such applications include, for example, electrical muscle stimulators and other nerve stimulators, sensory prosthetic devices, neural prosthetic devices, and functional electrical stimulation (FES) systems. It is considered to be within the scope of the present invention to configure the present invention to operate with such other devices.

As noted, embodiments of the present invention are described herein in connection with one embodiment of an exemplary implantable medical device, a prosthetic hearing device. Exemplary implantable hearing prostheses in which the present invention may be implemented include, but are not limited to, those systems described in U.S. Pat. Nos. 4,532,930, 6,537,200, 6,565,503, 6,575,894 and 6,697,674, the entire contents and disclosures of which are hereby incorporated by reference herein. As described therein, implantable hearing prostheses generally include an external, wearable control unit that determines a pattern of electrical stimulation that is provided to an implanted stimulator unit containing active circuitry, typically in a hermetic enclosure. Electrical stimulation channels are routed through electrodes to provide electrical stimulation of auditory nerve cells.

Figure 6A:
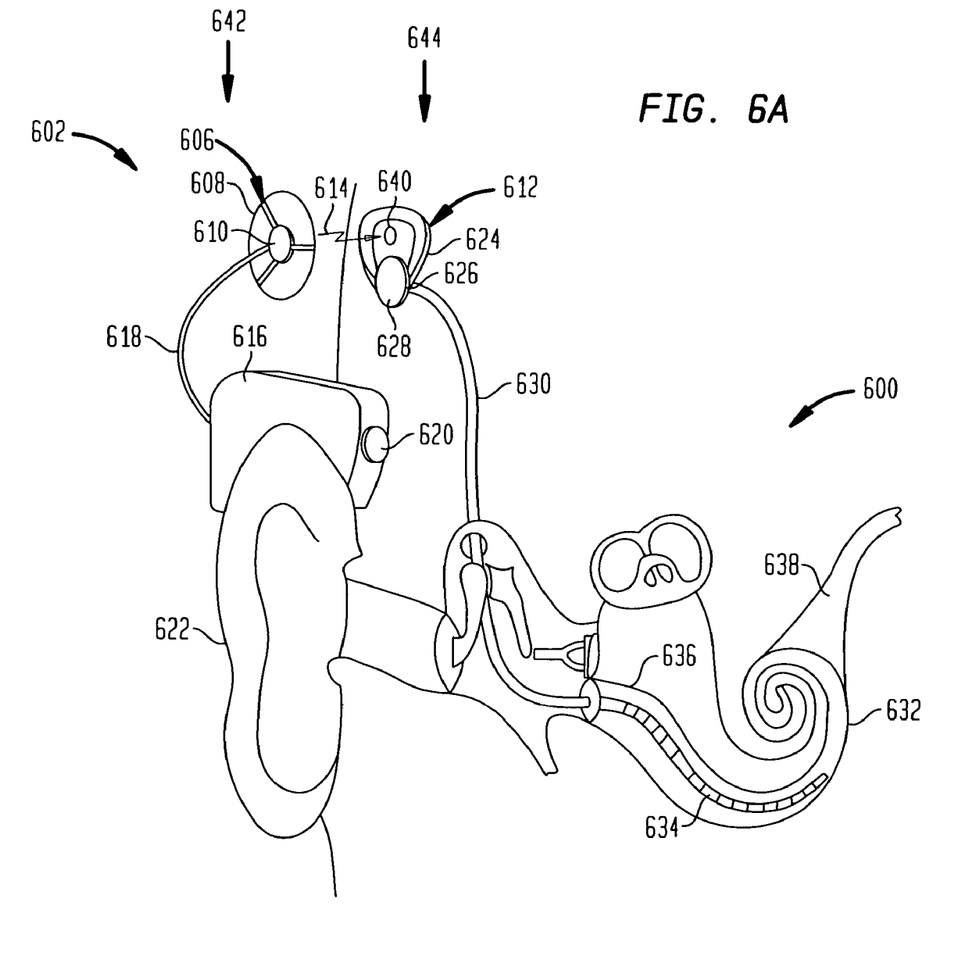
FIG. 6A is a schematic block diagram of one embodiment of an exemplary hearing prosthesis, specifically, a cochlear implant system, suitable for implementing embodiments of the present invention.

FIG. 6A is a schematic diagram of an exemplary prosthetic hearing device 600 in which embodiments of the present invention may be implemented. Prosthetic hearing device 600 comprises external components 642 which are directly or indirectly attached to the body of the recipient, and internal components 644 which are temporarily or permanently implanted in the recipient. External components 642 typically comprise a microphone 620 for detecting sounds, a speech processor 616 that converts the detected sounds into a coded stimulation signal, a power source (not shown), and an external transmitter unit 606. External transmitter unit 606 comprises an external coil 608 and a magnet 610 secured directly or indirectly to external coil 608. Speech processor 616 processes the output of microphone 620 that is positioned, in the depicted embodiment, on the ear 622 of the recipient. Speech processor 616 generates a coded stimulation signal which is provided to external transmitter unit 606 via cable 618.

Internal components 644 comprise an internal receiver unit 612, a stimulator unit 626, and an electrode array 634. Internal receiver unit 612 comprises an internal receiver coil 624 and a magnet 640 fixed relative to internal coil 624. Internal receiver unit 612 and stimulator unit 626 are hermetically sealed within a housing 628. Internal coil 624 receives power and data from transmitter coil 608. A cable 630 extends from stimulator unit 626 to cochlea 632 and terminates in an electrode array 634. The received signals are applied by array 634 to the basilar membrane 636 thereby stimulating the auditory nerve 638.

Collectively, transmitter antenna coil 608 (or more generally, external coil 608) and receiver antenna coil 624 (or, more generally internal coil 624) form an inductively-coupled coil system of a transcutaneous transfer apparatus 602. Transmitter antenna coil 608 transmits electrical signals to the implantable receiver coil 624 via a radio frequency (RF) link 614. Internal coil 624 is typically a wire antenna coil comprised of at least one and preferably multiple turns of electrically insulated single-strand or multi-strand platinum or gold wire. The electrical insulation of internal coil 624 is provided by a flexible silicone molding (not shown). In use, implantable receiver unit 612 can be positioned in a recess of the temporal bone adjacent ear 622 of the recipient.

Implantable receiver unit 612 has a magnet 640 embedded within the silicone housing of internal coil 624 to allow transcutaneous alignment of external coil 608 of external transmitter unit 606 and internal coil 624 of internal receiver unit 612. This magnetic transcutaneous alignment provides an attraction force that is designed to maintain external coil 608 in place on the head of the recipient without the necessity for any additional clips or other holding means. This magnetic transcutaneous alignment also facilitates the correct lateral alignment of external coil 608 over internal coil 624 to permit the efficient transmission of power and/or data.

Figure 6B:
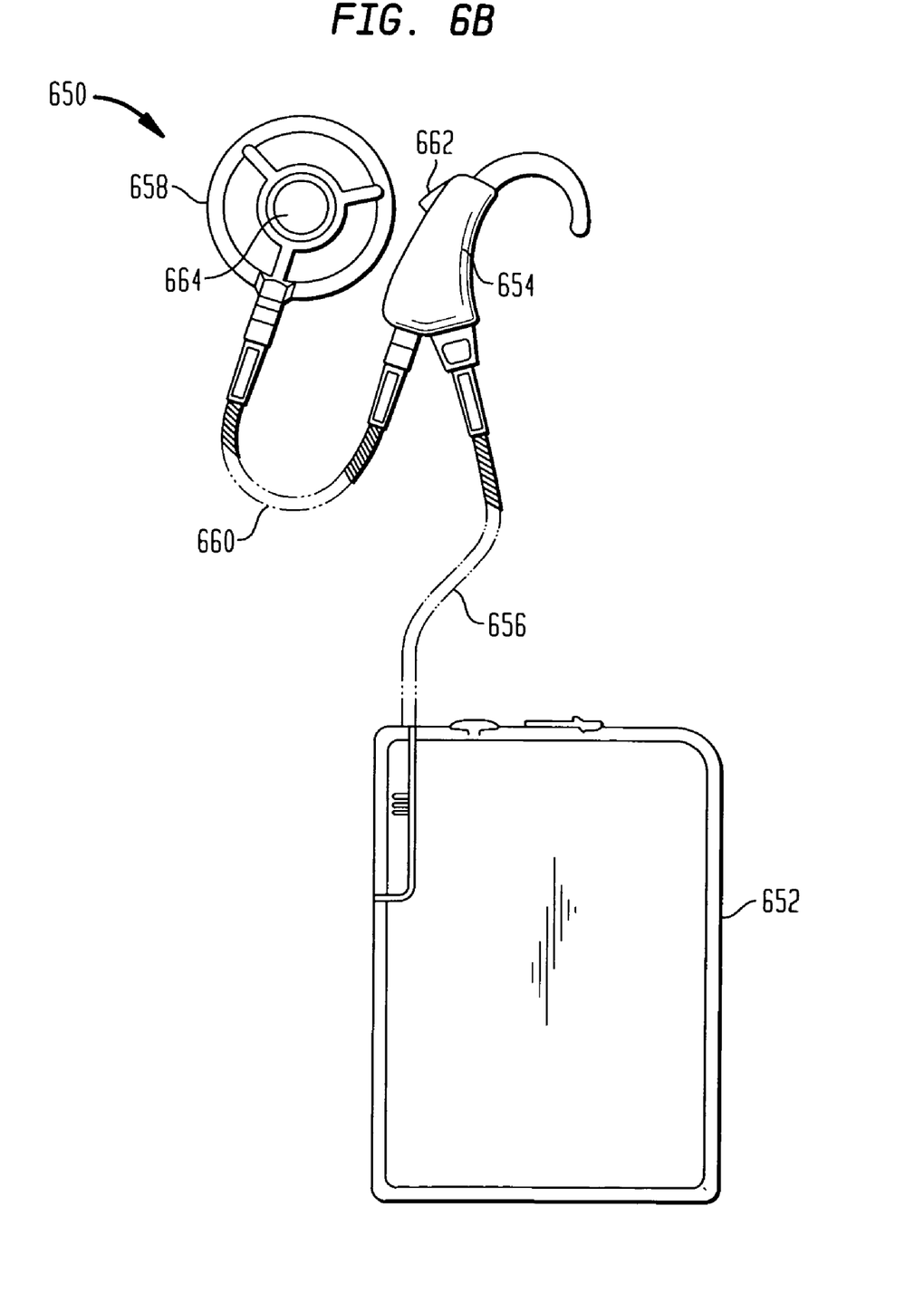
FIG. 6B is a schematic block diagram of an alternative embodiment of an exemplary acoustic prosthesis suitable for implementing embodiments of the present invention.

External assembly 642 of prosthetic hearing device 600 may have different configurations and arrangements. FIG. 6B is a perspective view of one embodiment of external assembly 642, referred to as external assembly arrangement 650. In arrangement 650, a body-worn speech processing unit 652 is connected to a headset unit 654 with a first cable 206. Headset unit 654 is, in turn, connected to a transmitter coil 658 with a second cable 210.

In this exemplary embodiment, headset unit 654 comprises three audio pickup devices 662. In one embodiment, audio pickup devices 662 are microphones, although in alternative embodiments audio pickup devices 662 can be telecoils or other similar devices now or later developed. Each audio pickup device 662 detects and converts ambient sound into an electrical audio signal. The electrical audio signals are transmitted over cable 656 to speech processing unit 652, which contains appropriate speech processing circuitry to convert the electrical audio signals into electrical coded stimulation signals according to a particular speech processing strategy. The stimulation signals are transmitted via cable 656 from speech processing unit 652 to headset unit 654, and from headset unit 654 to external coil 658 via cable 660, for transmission over an RF link to implanted stimulator unit 626 (FIG. 6A).

Although the present invention has been described with reference to an implantable device having an electrode carrier containing an electrode and an electrical conductor, any suitable components and/or configuration now or later known for signal communication may be utilized in the present invention.

Although the present invention has been fully described in conjunction with the certain embodiments thereof with reference to the accompanying drawings, it is to be understood that various changes and modifications may be apparent to those skilled in the art. For example, embodiments of the present invention have been described in connection with a prosthetic hearing device. As noted, the present invention may be implemented in any electrical stimulating device now or later developed. The present invention is particularly beneficial when implemented in medical devices. Such applications include the above noted electrical muscle stimulators and other nerve stimulators, sensory prosthetic devices, neural prosthetic devices, and functional electrical stimulation (FES) systems, for example. It is considered to be within the scope of the present invention to configure the present invention to operate with such other devices. Such changes and modifications are to be understood as included within the scope of the present invention.

What is claimed is:

1. An implantable device comprising:
   an elongate electrode carrier comprising a plurality of closed breaks disposed in a surface of said carrier, wherein said one or more closed breaks are configured to promote flexibility of said carrier, and further wherein said closed breaks comprise a first material different from a second material of said electrode carrier, said first material being disposed within one or more regions of said electrode carrier where only portions of said electrode carrier are absent; and
   a plurality of electrodes mounted in said carrier.

2. The implantable device of claim 1, wherein at least one of said closed breaks is disposed along a circumference of said carrier.

3. The implantable device of claim 2, wherein at least one of said closed breaks is configured to define a corrugated surface on the surface of said carrier.

4. The implantable device of claim 2, wherein at least one of said closed breaks is configured to have the shape of a helix around the longitudinal axis of said elongate electrode carrier.

5. The implantable device of claim 2, wherein at least one of said closed breaks is further configured to have a cross-sectional shape across the longitudinal axis of said elongate electrode carrier that is one of either a "v" shape, a "u" shape, and an "x" shape.

6. The implantable device of claim 1, wherein at least one of said closed breaks is filled with the first material of higher flexibility than the second material of said carrier.

7. The implantable device of claim 1, wherein said closed breaks are incorporated in said carrier prior to assembly of said carrier.

8. The implantable device of claim 1, wherein said closed breaks are incorporated in said carrier subsequent to assembly of said carrier.

9. The implantable device of claim 1, wherein the implantable device is a prosthetic hearing device.

10. The implantable device of claim 9, wherein the prosthetic hearing device is an implantable cochlear prosthesis.

11. The implantable device of claim 1, wherein at least one of said closed breaks is configured to define a corrugated surface on the surface of said carrier.

12. The implantable device of claim 1, wherein at least one of the closed breaks is disposed in the carrier opposite one of the electrodes.

13. An implantable device comprising:
an elongate electrode carrier comprising a plurality of breaks disposed in a surface of said carrier, wherein said surface is substantially continuous and said one or more breaks are configured to promote flexibility of said carrier during flexing of said carrier, and further wherein said closed breaks comprise a first material different from a second material of said electrode carrier, said first material being disposed within one or more regions of said electrode carrier where only portions of said electrode carrier are absent; and
a plurality of electrodes mounted in said carrier, wherein more than one of the breaks are disposed between adjacent electrodes.

14. The implantable device of claim 13, wherein at least one of said breaks is disposed along a circumference of said carrier.

15. The implantable device of claim 14, wherein at least one of said breaks is a linear slit.

16. The implantable device of claim 14, wherein at least one of said breaks is configured to have the shape of a helix around the longitudinal axis of said elongate electrode carrier.

17. The implantable device of claim 13, wherein the implantable device is a prosthetic hearing device.

18. The implantable device of claim 17, wherein the prosthetic hearing device is an implantable cochlear prosthesis.

19. The implantable device of claim 13, wherein said breaks are incorporated in said carrier prior to assembly of said carrier.

20. The implantable device of claim 13, wherein said breaks are incorporated in said carrier subsequent to assembly of said carrier.

21. The implantable device of claim 13, wherein at least one of the breaks is disposed in the carrier opposite one of the electrodes.

22. A method of manufacturing an implantable device having an electrode carrier with a longitudinal axis, comprising:
forming the carrier;
mounting a plurality of electrodes in the carrier; and
forming a plurality of breaks in a surface of the carrier, wherein said surface is substantially continuous, the at least one break is configured to promote flexibility of said carrier, the closed breaks comprise a first material different from a second material of said electrode carrier, said first material being disposed within one or more regions of said electrode carrier where only portions of said electrode carrier are absent, and more than one of the breaks are disposed between adjacent electrodes.

23. The method of claim 22, wherein said forming the breaks is performed during said forming of the carrier.

24. The method of claim 22, wherein said forming the carrier further comprises:
molding the carrier.

25. The method of claim 22, wherein said forming the breaks further comprises:
cutting a surface of the carrier to form the at least one break.

26. The method of claim 22, wherein said forming the breaks further comprises:
forming at least one of the breaks along a circumference of said carrier.

27. The method of claim 26, wherein said forming at least one of the breaks along a circumference further comprises:
forming the break in the shape of a helix around the longitudinal axis of said elongate electrode carrier.

28. The method of claim 26, wherein said forming at least one of the breaks along a circumference further comprises:
forming the break as a linear slit.

29. The method of claim 22, wherein said forming the breaks further comprises forming at least one of the breaks in the carrier opposite one of the electrodes.

30. An implantable device comprising:
an elongate electrode carrier comprising a plurality of flexing means for promoting flexibility of said carrier during flexing of said carrier, wherein the plurality of flexing means are disposed in a substantially continuous surface of said carrier, and further wherein said plurality of flexing means comprise a first material different from a second material of said electrode carrier, said first material being disposed within one or more regions of said electrode carrier where only portions of said electrode carrier are absent; and
a plurality of means for stimulating tissue mounted in said carrier, wherein more than one of the flexing means is disposed between adjacent means for stimulating tissue.

31. The implantable device of claim 30, wherein at least one of said flexing means is disposed along a circumference of said carrier.

32. The implantable device of claim 30, wherein the implantable device is a prosthetic hearing device.

33. The implantable device of claim 32, wherein the prosthetic hearing device is an implantable cochlear prosthesis.

34. The implantable device of claim 30, wherein at least one of the closed breaks is disposed in the carrier opposite one of the electrodes.

35. An implantable device comprising:
an elongate electrode carrier comprising a plurality of closed flexing means for promoting flexibility by said carrier during flexing of said carrier, wherein the plurality of flexing means are disposed in a surface of said carrier, and further wherein said plurality of flexing means comprise a first material different from a second material of said electrode carrier, said first material being disposed within one or more regions of said electrode carrier where only portions of said electrode carrier are absent; and
a plurality of means for stimulating tissue mounted in said carrier, wherein more than one of the flexing means is disposed between adjacent means for stimulating tissue.

36. The implantable device of claim 35, wherein at least one of said closed flexing means is disposed along a circumference of said carrier.

37. The implantable device of claim 35, wherein at least one of the closed breaks is disposed in the carrier opposite one of the electrodes.

38. A method of manufacturing an implantable device having an electrode carrier with a longitudinal axis, comprising:
forming the carrier;
mounting a plurality of electrodes in the carrier; and
forming a plurality of closed breaks in a surface of the carrier, wherein the closed breaks are configured to promote flexibility of said carrier, the closed breaks comprise a first material different from a second material of said electrode carrier, said first material being disposed within one or more regions of said electrode carrier where only portions of said electrode carrier are absent, and more than one of the closed breaks are disposed between adjacent electrodes.

39. The method of claim 38, wherein said forming the closed breaks is performed during said forming of the carrier.

40. The method of claim 38, wherein at least one of said closed breaks is disposed along a circumference of said carrier.

41. The method of claim 40, wherein at least one of said closed breaks is configured to define a corrugated surface on the surface of said carrier.

42. The method of claim 40, wherein at least one of said closed breaks is configured to have the shape of a helix around the longitudinal axis of said elongate electrode carrier.

43. The method of claim 40, wherein at least one of said closed breaks is further configured to have a cross-sectional shape across the longitudinal axis of said elongate electrode carrier that is one of either a "v" shape, a "u" shape, and an "x" shape.

44. The method of claim 38, wherein said forming the closed breaks further comprises forming at least one of the closed breaks in the carrier opposite one of the electrodes.

* * * * *